(12) United States Patent
Kikugawa et al.

(10) Patent No.: US 8,633,135 B2
(45) Date of Patent: Jan. 21, 2014

(54) HERBICIDAL COMPOSITION

(75) Inventors: Hiroshi Kikugawa, Osaka (JP); Tomoaki Kezuka, Osaka (JP); Ryu Yamada, Kusatsu (JP); Takashi Terada, Kusatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 13/700,769

(22) PCT Filed: Jun. 8, 2011

(86) PCT No.: PCT/JP2011/063625
§ 371 (c)(1),
(2), (4) Date: Nov. 29, 2012

(87) PCT Pub. No.: WO2011/158843
PCT Pub. Date: Dec. 22, 2011

(65) Prior Publication Data
US 2013/0085065 A1    Apr. 4, 2013

(30) Foreign Application Priority Data

Jun. 14, 2010 (JP) ................................. 2010-135400
Oct. 12, 2010 (JP) ................................. 2010-229645

(51) Int. Cl.
*A01N 43/60* (2006.01)
(52) U.S. Cl.
USPC ...................................................... 504/136
(58) Field of Classification Search
None
See application file for complete search history.

(56) References Cited

U.S. PATENT DOCUMENTS

2009/0069346 A1    3/2009   Ishihara et al.

FOREIGN PATENT DOCUMENTS

WO    2007/105377    9/2007
WO    2009/054823    4/2009

OTHER PUBLICATIONS

Alberto et al., "Sugarcane Tolerance to Flazasulfuron in Isolated and Sequential Aplications and in a Mixture With Others Herbicides, and Its Effects for Controlling *Cyperus rotundus* L. and Also Other Species of Weeds", Revista Ceres, vol. 43, No. 245, 1996, pp. 102-111 (English language abstract at end).
International Preliminary Report on Patentability and Written Opinion of the Searching Authority for International Application No. PCT/JP2011/06325, 2011.
Search report from and Written Opinion of the Searching Authority for International Application No. PCT/JP2011/06325, 2011.

*Primary Examiner* — Alton Pryor
(74) *Attorney, Agent, or Firm* — Greenblum & Bernstein, P.L.C.

(57) ABSTRACT

At present, many herbicidal compositions have been developed and used, but there are a variety of types of weeds to be controlled, and their development lasts for a long period of time. Thus, a high active and long-residual herbicidal composition having a broad herbicidal spectrum has been desired. The present invention provides a synergistic herbicidal composition comprising (A) flazasulfuron or its salt and (B) at least one urea compound selected from the group consisting of tebuthiuron, diuron and metobromuron or its salt. According to the synergistic herbicidal composition of the present invention, a high active and long-residual herbicidal composition having a broad-spectrum can be provided.

8 Claims, No Drawings

HERBICIDAL COMPOSITION

TECHNICAL FIELD

The present invention relates to a synergistic herbicidal composition comprising (A) flazasulfuron or its salt (hereinafter referred to as compound A) and (B) at least one urea compound selected from the group consisting of tebuthiuron, diuron and metobromuron or its salt (hereinafter referred to as compound B).

BACKGROUND ART

Various herbicidal compositions have been studied to control undesired plants (hereinafter simply referred to as weeds) in agricultural fields and non-crop land. For example, Patent Document 1 discloses a mixture comprising a sulfonylurea herbicide, diuron and hexadinone. However, Patent Document 1 failed to specifically disclose a synergistic herbicidal composition comprising compounds A and B. Further, Non-Patent Document 1 discloses influences over cultivation of sugarcane by mixed use of flazasulfuron and diuron. However, Non-Patent Document 1 failed to disclose whether a synergistic herbicidal effect is obtained when they are used in combination.

PRIOR ART DOCUMENTS

Patent Document

Patent Document 1: WO2009/054823

Non-Patent Document

Non-Patent Document 1: Revista Ceres, 43(245), p. 102-111, 1996

DISCLOSURE OF INVENTION

Technical Problem

At present, many herbicidal compositions have been developed and used, but there are a variety of types of weeds to be controlled, and their development lasts for a long period of time. Thus, a high active and long-residual herbicidal composition having a broad herbicidal spectrum has been desired.

Solution to Problem

By combining compound A and compound B, a high active and long-residual herbicidal composition having a broad herbicidal spectrum can be provided.

Advantageous Effects of Invention

According to the present invention, a high active and long-residual herbicidal composition having a broad herbicidal spectrum, with which the dose of the active ingredient can be reduced, can be provided.

DESCRIPTION OF EMBODIMENTS

In compound A, flazasulfuron (common name) is 1-(4,6-dimethoxypyrimidin-2-yl)-3-(3-trifluoromethyl-2-pyridylsulfonyl)urea.

In compound B, tebuthiuron (common name) is 1-(5-tertiarybutyl-1,3,4-thiadiazol-2-yl)-1,3-dimethylurea, diuron (common name) is 3-(3,4-dichlorophenyl)-1,1-dimethylurea, and metobromuron (common name) is 3-(4-bromophenyl)-1-methoxy-1-methylurea. Among them, tebuthiuron or metobromuron is preferred.

The salt included in compound A and compound B may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of compound A to compound B cannot generally be defined, as it varies depending upon various conditions such as the type of the formulation, the weather conditions, and the type and the growth stage of the weeds to be controlled, and is, for example, from 1:1 to 1:500, preferably from 1:3 to 1:200, particularly preferably from 1:10 to 1:150 by the weight ratio.

The dose of compound A and compound B cannot generally be defined, as it varies depending upon the various conditions such as the mixing ratio of compound A to compound B, the type of the formulation, the weather conditions, and the type and the growth stage of the weeds to be controlled. However, for example, compound A is applied in an amount of from 10 to 150 g/ha, preferably from 15 to 100 g/ha, particularly preferably from 20 to 50 g/ha, and compound B is applied in an amount of from 150 to 5,000 g/ha, preferably from 300 to 3,000 g/ha, particularly preferably from 500 to 3,000 g/ha.

The herbicidal composition of the present invention may be applied to weeds or may be applied to a place where they grow. Further, it may be applied at any time either before or after the emergence of the weeds. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf course, vacant land, forests, factory sites, railway sides and roadsides.

The herbicidal composition of the present invention can control a broad range of weeds such as annual weeds and perennial weeds. The weeds to be controlled by the herbicidal composition of the present invention may, for example, be cyperaceae such as green kyllinga (*Cyperus brevifolia* var. leiolepis), purple nutsedge (*Cyperus rotundus* L.), and amur cyperus (*Cyperus microiria* Steud.); gramineae such as barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), goosegrass (*Eleusine indica* L.), johnsongrass (*Sorghum halepense* L.), annual bluegrass (*Poa annua* L.), panic grasses (*Panicum* spp.), guineagrass (*Panicum maximum* Jacq.), marmeladegrass or signalgrass (*Brachiaria* spp.), surinam grass (*Brachiaria decumbens* Stapf.), paspalum (*Paspalum* spp.), and itchgrass (*Rottboellia cochinchinensis* (LOUR.) W. D.CLAYTON); scrophulariaceae such as persian speedwell (*Veronica persica* Poir.), and corn speedwell (*Veronica arvensis* L.); compositae such as beggarticks (*Bidens* spp.), hairy fleabane (*Conyza bonariensis* (L.) Cronq.), horseweed (*Erigeron canadensis* L.), dandelion (*Taraxacum officinale* Weber), and common cocklebur (*Xanthium strumarium* L.); leguminosae such as white clover (*Trifolium repens* L.); caryophyllaceae such as sticky chickweed (*Cerastium glomeratum* Thuill.), and common chickweed (*Stellaria media* L.); euphorbiaceae such as garden spurge (*Euphorbia hirta* L.), and threeseeded copperleaf (*Acalvpha australis*L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); qeraniaceae such as carolina geranium (*Geranium carolinianum* L.); labiatae such as purple deadnettle (*Lamium purpureum* L.), and henbit (*Lamium amplexicaule* L.); malvaceae such as velvetleaf (*Abutilon theophrasti* MEDIC.), and prickly sida (*Sida spinosa* L); convolvulaceae such as tall morningglory (*Ipomoea purpurea* L.), and field bindweed (*Convolvulus arvensis* L.); chenopodiaceae such as common lambsquarters (*Chenopodium album* L.); portulacaceae such as common purslane (*Portulaca oleracea* L.); amaranthaceae such as redroot pigweed (*Amaranthus retroflexus* L.); solanaceae such as black nightshade (*Solanum nigrum* L.); polygonaceeae such as spotted knotweed (*Polygonum lapathifolium* L.), and green smartweed (*Polygonum scabrum* MOENCH); and cruciferae such as flexuous bittercress (*Cardamine flexuosa* WITH.).

The herbicidal composition of the present invention can control weeds against which flazasulfuron may sometimes has no sufficient controlling effect depending upon various conditions such as the weather conditions and the growth stage of the weeds. For example, flazasulfuron has sometimes no sufficient controlling effect against some weeds included in solanaceae, scrophulariaceae and gramineae depending upon various conditions such as the weather conditions and the growth stage of the weeds. However, the herbicidal composition of the present invention comprising flazasulfuron and compound B in combination has excellent effects to control these weeds or to inhibit their growth.

The herbicidal composition of the present invention may further be mixed with other herbicidal active ingredients, whereby the spectrum of weeds to be controlled, the application timing, the herbicidal activity, etc. can be improved to preferred directions in some cases. Such other herbicidal active ingredients (common names, etc.) may, for example, be 2,4-D, dicamba, aminopyralid, simazine, atrazine, hexazinone, metribuzin, ametryn, indaziflam, amicarbazone, paraquat, oxyfluorfen, flumioxazin, fluthiacet-methyl, sulfentrazone, butafenacil, saflufenacil, norflurazon, clomazone, mesotrione, bicyclopyrone, fluazifop, sulfometuron, rimsulfuron, nicosulfuron, imazosulfuron, halosulfuron, pyroxsulam, glyphosate, glufosinate, trifluralin, oryzalin, pendimethalin, methyldymron, asulam, aminocyclopyrachlor, ethyl [3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523), or [(5-(2,6-difluorobenzyl)oxymethyl-5-methyl-3-(3-methylthiophen-2-yl)-1,2-isoxazoline (MRC-01). In a case where salts, alkyl esters, hydrates, different crystal forms and various structural isomers, etc. exist as these compounds, they are, of course, all included, even when not specifically mentioned.

The herbicidal composition of the present invention may be prepared by mixing compound A and compound B, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A and compound B may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives may be from 0.001:99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the weeds to be controlled, and for example, the following methods may be mentioned.

1. Compound A and compound B are formulated together, and the formulation is applied as it is.

2. Compound A and compound B are formulated together, the formulation is diluted to a predetermined concentration with e.g. water, and as the case requires, a spreader (such as a surfactant, a vegetable oil or a mineral oil) is added for application.

3. Compound A and compound B are separately formulated and applied as they are.

4. Compound A and compound B are separately formulated, and they are diluted to a predetermined concentration with e.g. water, and as the case requires, a spreader (such as a surfactant, a vegetable oil or a mineral oil) is added for application. 5. Compound A and compound B are separately formulated, and the formulations are mixed when diluted to a predetermined concentration with e.g. water, and as the case requires, a spreader (such as a surfactant, a vegetable oil or a mineral oil) is added for application.

Preferred embodiments of the present invention will be described below, but the present invention is by no means restricted thereto.

(1) A synergistic herbicidal composition comprising (A) flazasulfuron or its salt and (B) tebuthiuron or its salt.

(2) The composition according to the above (1), wherein the mixing ratio of (A) flazasulfuron or its salt to (B) tebuthiuron or its salt is from 1:3 to 1:50 by the weight ratio.

(3) The composition according to the above (1), wherein the mixing ratio of (A) flazasulfuron or its salt to (B) tebuthiuron or its salt is from 1:4 to 1:50 by the weight ratio.

(4) The composition according to the above (1), wherein the mixing ratio of (A) flazasulfuron or its salt to (B) tebuthiuron or its salt is from 1:10 to 1:40 by the weight ratio.

(5) A method for controlling undesired plants or inhibiting their growth, which comprises applying an effective amount of a synergistic herbicidal composition comprising (A) flazasulfuron or its salt and (B) tebuthiuron or its salt to the undesired plants or to a place where they grow.

(6) A method for controlling undesired plants or inhibiting their growth, which comprises applying a synergistic herbicidally effective amount of (A) flazasulfuron or its salt and (B) tebuthiuron or its salt, to the undesired plants or to a place where they grow. (7) The method according to the above (5) or (6), wherein (A) flazasulfuron or its salt is applied in an amount of from 20 to 100 g/ha, and (B) tebuthiuron or its salt is applied in an amount of from 300 to 1,000 g/ha. (8) The method according to the above (5) or (6), wherein (A) flazasulfuron or its salt is applied in an amount of from 20 to 75 g/ha, and (B) tebuthiuron or its salt is applied in an amount of from 300 to 1,000 g/ha.

(9) The method according to the above (5) or (6), wherein (A) flazasulfuron or its salt is applied in an amount of from 25 to 50 g/ha, and (B) tebuthiuron or its salt is applied in an amount of from 500 to 1,000 g/ha.

(10) A synergistic herbicidal composition comprising (A) flazasulfuron or its salt and (B) diuron or its salt.

(11) The composition according to the above (10), wherein the mixing ratio of (A) flazasulfuron or its salt to (B) diuron or its salt is from 1:6.6 to 1:200 by the weight ratio.

(12) The composition according to the above (10), wherein the mixing ratio of (A) flazasulfuron or its salt to (B) diuron or its salt is from 1:10 to 1:125 by the weight ratio. (13) The composition according to the above (10), wherein the mixing ratio of (A) flazasulfuron or its salt to (B) diuron or its salt is from 1:22 to 1:66.6 by the weight ratio.

(14) A method for controlling undesired plants or inhibiting their growth, which comprises applying an effective amount of a synergistic herbicidal composition comprising (A) flazasulfuron or its salt and (B) diuron or its salt to the undesired plants or to a place where they grow.

(15) A method for controlling undesired plants or inhibiting their growth, which comprises applying a synergistic herbicidally effective amount of (A) flazasulfuron or its salt and (B) diuron or its salt, to the undesired plants or to a place where they grow.

(16) The method according to the above (14) or (15), wherein (A) flazasulfuron or its salt is applied in an amount of from 20 to 75 g/ha, and (B) diuron or its salt is applied in an amount of from 500 to 4,000 g/ha.

(17) The method according to the above (14) or (15), wherein (A) flazasulfuron or its salt is applied in an amount of from 20 to 50 g/ha, and (B) diuron or its salt is applied in an amount of from 500 to 2,500 g/ha.

(18) The method according to the above (14) or (15), wherein (A) flazasulfuron or its salt is applied in an amount of from 30 to 50 g/ha, and (B) diuron or its salt is applied in an amount of from 1,100 to 2,000 g/ha.

(19) A synergistic herbicidal composition comprising (A) flazasulfuron or its salt and (B) metobromuron or its salt.

(20) The composition according to the above (19), wherein the mixing ratio of (A) flazasulfuron or its salt to (B) metobromuron or its salt is from 1:2 to 1:200 by the weight ratio.

(21) The composition according to the above (19), wherein the mixing ratio of (A) flazasulfuron or its salt to (B) metobromuron or its salt is from 1:10 to 1:150 by the weight ratio.

(22) The composition according to the above (19), wherein the mixing ratio of (A) flazasulfuron or its salt to (B) metobromuron or its salt is from 1:15 to 1:100 by the weight ratio.

(23) A method for controlling undesired plants or inhibiting their growth, which comprises applying an effective amount of a synergistic herbicidal composition comprising (A) flazasulfuron or its salt and (B) metobromuron or its salt to the undesired plants or to a place where they grow.

(24) A method for controlling undesired plants or inhibiting their growth, which comprises applying a synergistic herbicidally effective amount of (A) flazasulfuron or its salt and (B) metobromuron or its salt, to the undesired plants or to a place where they grow.

(25) The method according to the above (23) or (24), wherein (A) flazasulfuron or its salt is applied in an amount of from 20 to 75 g/ha, and (B) metobromuron or its salt is applied in an amount of from 150 to 4,000 g/ha.

(26) The method according to the above (23) or (24), wherein (A) flazasulfuron or its salt is applied in an amount of from 20 to 50 g/ha, and (B) metobromuron or its salt is applied in an amount of from 500 to 3,000 g/ha.

(27) The method according to the above (23) or (24), wherein (A) flazasulfuron or its salt is applied in an amount of from 30 to 50 g/ha, and (B) metobromuron or its salt is applied in an amount of from 750 to 3,000 g/ha.

EXAMPLES

Now, the present invention will be described in further detail with reference to Examples. However, it should be understood that the present invention is by no means restricted to such specific Examples.

Test Example 1

Upland field soil was put into a $1/1,000,000$ ha pot, and seeds of various plants were sown. When the plants reached certain leaf stages (guineagrass (*Panicum maximum* Jacq.): 4.5 to 5.0 leaf stage, crabgrass (*Digitaria ciliaris* (Retz.) Koel): 3.0 to 4.2 leaf stage), a predetermined amount of each herbicidal composition was diluted with water (corresponding to 200 L/ha) containing 0.25 vol % of an agricultural adjuvant (tradename: Agral, manufactured by Syngenta) and applied by foliar application with a small sprayer.

On the 28th day after application, the state of growth of the plants were visually observed and evaluated in accordance with the following evaluation standard. The growth inhibition rate (%) (measured value) and the growth inhibition rate (%) (calculated value) calculated by the Colby's formula are shown in Tables 1 and 2.

Growth inhibition rate (%)=
0:equivalent to the non-treated area to 100:complete kill

TABLE 1

| Active ingredient | Dose (g/ha) | Growth inhibition rate (%) of guineagrass | |
|---|---|---|---|
| | | Measured value | Calculated value |
| Flazasulfuron | 20 | 90 | — |
| | 37.5 | 92 | — |
| Tebuthiuron | 500 | 15 | — |
| Flazasulfuron + Tebuthiuron | 20 + 500 | 95 | 92 |
| | 37.5 + 500 | 98 | 93 |

TABLE 2

| Active ingredient | Dose (g/ha) | Growth inhibition rate (%) of crabgrass | |
|---|---|---|---|
| | | Measured value | Calculated value |
| Flazasulfuron | 25 | 40 | — |
| Tebuthiuron | 500 | 0 | — |
| Flazasulfuron + Tebuthiuron | 25 + 500 | 84 | 40 |

Test Example 2

Upland field soil was put into a 1/1,000,000 ha pot, and seeds of surinam grass (*Brachiaria decumbens* Stapf.) were sown. When the surinam grass reached 2.8 to 3.2 leaf stage, a predetermined amount of each herbicidal composition was diluted with water (corresponding to 200 L/ha) containing 0.25 vol % of an agricultural adjuvant (tradename: Agral, manufactured by Syngenta) and applied by foliar application with a small sprayer.

On the 28th day after application, the state of growth of the plant was visually observed. The growth inhibition rates (%) obtained in the same manner as in the above Test Example 1 are shown in Table 3.

TABLE 3

| Active ingredient | Dose (g/ha) | Growth inhibition rate (%) of surinam grass | |
|---|---|---|---|
| | | Measured value | Calculated value |
| Flazasulfuron | 37.5 | 45 | — |
| Diuron | 1250 | 0 | — |
| Flazasulfuron + Diuron | 37.5 + 1250 | 74 | 45 |

Test Example 3

Upland field soil was put into a 1/1,000,000 ha pot, and seeds of surinam grass (*Brachiaria decumbens* Stapf.) were sown. On the day after application, a predetermined amount of each herbicidal composition was diluted with water corresponding to 200 L/ha and applied by soil application with a small sprayer.

On the 42nd day after application, the state of growth of the plant was visually observed. The growth inhibition rates (%) obtained in the same manner as in the above Test Example 1 are shown in Table 4.

TABLE 4

| Active ingredient | Dose (g/ha) | Growth inhibition rate (%) of surinam grass | |
|---|---|---|---|
| | | Measured value | Calculated value |
| Flazasulfuron | 25 | 70 | — |
| Tebuthiuron | 500 | 28 | — |
| Flazasulfuron + Tebuthiuron | 25 + 500 | 99 | 78 |

Test Example 4

Upland field soil was put into a 1/1,000,000 ha pot, and seeds of field bindweed (*Convolvulus arvensis* L.) were sown. On the day after application, a predetermined amount of each herbicidal composition was diluted with water corresponding to 200 L/ha and applied by soil application with a small sprayer.

On the 42nd day after application, the state of growth of the plant was visually observed. The growth inhibition rates (%) obtained in the same manner as in the above Test Example 1 are shown in Table 5.

TABLE 5

| Active ingredient | Dose (g/ha) | Growth inhibition rate (%) of field bindweed | |
|---|---|---|---|
| | | Measured value | Calculated value |
| Flazasulfuron | 37.5 | 25 | — |
| Diuron | 1250 | 0 | — |
| Flazasulfuron + Diuron | 37.5 + 1250 | 55 | 25 |

Test Example 5

Upland field soil was put into a 1/1,000,000 ha pot, and seeds of crabgrass (*Digitaria ciliaris* (Retz.) Koel) were sown. When crabgrass reached 3.0 to 4.2 leaf stage, a predetermined amount of each herbicidal composition was diluted with water (corresponding to 200 L/ha) containing 0.2 vol % of an agricultural adjuvant (tradename: MonFast, manufactured by Monsanto) and applied by foliar application with a small sprayer.

On the 28th day after application, the state of growth of the plant was visually observed. The growth inhibition rates (%) obtained in the same manner as in the above Test Example 1 are shown in Table 6.

TABLE 6

| Active ingredient | Dose (g/ha) | Growth inhibition rate (%) of crabgrass | |
|---|---|---|---|
| | | Measured value | Calculated value |
| Flazasulfuron | 30 | 50 | — |
| | 40 | 58 | — |
| Metobromuron | 500 | 0 | — |
| | 1000 | 0 | — |
| Flazasulfuron + Metobromuron | 30 + 500 | 70 | 50 |
| | 30 + 1000 | 70 | 50 |
| | 40 + 500 | 63 | 58 |
| | 40 + 1000 | 65 | 58 |

Test Example 6

Upland field soil was put into a 1/1,000,000 ha pot, and seeds of crabgrass (*Digitaria ciliaris* (Retz.) Koel) were sown.

When crabgrass reached 3.8 to 4.0 leaf stage, a predetermined amount of each herbicidal composition was diluted with water (corresponding to 200 L/ha) containing 0.25 vol % of an agricultural adjuvant (tradename: Agral, manufactured by Syngenta) and applied by foliar application with a small sprayer.

On the 28th day after application, the state of growth of the plant was visually observed. The growth inhibition rates (%) obtained in the same manner as in the above Test Example 1 are shown in Table 7.

TABLE 7

| Active ingredient | Dose (g/ha) | Growth inhibition rate (%) of crabgrass | |
|---|---|---|---|
| | | Measured value | Calculated value |
| Flazasulfuron | 15 | 40 | — |
| Diuron | 3000 | 80 | — |
| Flazasulfuron + Diuron | 15 + 3000 | 100 | 88 |

Test Example 7

Upland field soil was put into a 1/1,000,000 ha pot, and seeds of crabgrass (*Digitaria ciliaris* (Retz.) Koel) were sown. When crabgrass reached 4.5 leaf stage, a predetermined amount of each herbicidal composition was diluted with water (corresponding to 200 L/ha) containing 0.25 vol % of an agricultural adjuvant (tradename: Agral, manufactured by Syngenta) and applied by foliar application with a small sprayer.

On the 28th day after application, the state of growth of the plant was visually observed. The growth inhibition rates (%) obtained in the same manner as in the above Test Example 1 are shown in Table 8.

TABLE 8

| Active ingredient | Dose (g/ha) | Growth inhibition rate (%) of crabgrass | |
|---|---|---|---|
| | | Measured value | Calculated value |
| Flazasulfuron | 100 | 73 | — |
| Tebuthiuron | 300 | 17 | — |
| Metobromuron | 300 | 5 | — |
| Flazasulfuron + Tebuthiuron | 100 + 300 | 82 | 78 |
| Flazasulfuron + Metobromuron | 100 + 300 | 88 | 74 |

TABLE 8-continued

| Active ingredient | Dose (g/ha) | Growth inhibition rate (%) of crabgrass | |
|---|---|---|---|
| | | Measured value | Calculated value |

Industrial Applicability

According to the present invention, a high active and long-residual herbicidal composition having a broad-spectrum can be provided.

The entire disclosures of Japanese Patent Application No. 2010-135400 filed on Jun. 14, 2010 and Japanese Patent Application No. 2010-229645 filed on Oct. 12, 2010 including specifications, claims and summaries are incorporated herein by reference in their entireties.

The invention claimed is:

1. A synergistic herbicidal composition comprising (A) flazasulfuron or its salt and (B) at least one urea compound selected from the group consisting of tebuthiuron metobromuron, and salts of either of the foregoing.

2. The synergistic herbicidal composition according to claim 1, wherein the mixing ratio of (A) to (B) is from 1:1 to 1:50 for tebuthiuron or its salt as (B), or 1:1 to 1:100 for metobromuron or its salt as (B), by the weight ratio.

3. The synergistic herbicidal composition according to claim 2, wherein the mixing ratio of (A) to (B) is from 1:3 to 1:50 for tebuthiuron or its salt as (B), or 1:15 to 1:100 for metobromuron or its salt as (B), by the weight ratio.

4. A method for controlling undesired plants or inhibiting their growth, which comprises applying a synergistic herbicidally effective amount of (A) flazasulfuron or its salt and (B) at least one urea compound selected from the group consisting of tebuthiuron, metobromuron, and salts of either of the foregoing, to the undesired plants or to a place where they grow.

5. The method according to claim 4, wherein (A) is applied in an amount of from 20 to 100 g/ha, and (B) is tebuthiuron and is applied in an amount of from 300 to 1,000 g/ha.

6. The method according to claim 5, wherein (A) is applied in an amount of from 20 to 75 g/ha, and (B) is applied in an amount of from 300 to 1,000 g/ha.

7. The method according to claim 4, wherein (A) is applied in an amount of from 20 to 75 g/ha, and (B) is metobromuron and is applied in an amount of from 150 to 2,000 g/ha.

8. The method according to claim 7, wherein (A) is applied in an amount of from 20 to 50 g/ha, and (B) is applied in an amount of from 500 to 2,000 g/ha.

* * * * *